United States Patent [19]

Grollier et al.

[11] Patent Number: 4,657,690

[45] Date of Patent: Apr. 14, 1987

[54] WASHING AND FOAMING COMPOSITION BASED ON NON-IONIC SURFACE-ACTIVE AGENTS AND ANIONIC POLYMERS

[75] Inventors: Jean F. Grollier, Paris; Claude Dubief, Le Chesnay, both of France

[73] Assignee: L'Oreal, Paris, France

[21] Appl. No.: 599,975

[22] Filed: Apr. 13, 1984

[30] Foreign Application Priority Data

Apr. 15, 1983 [LU] Luxembourg ............................ 84753

[51] Int. Cl.$^4$ ........................ C11D 1/835; C11D 3/37
[52] U.S. Cl. .................................. 252/90; 252/174.21; 252/174.22; 252/174.23; 252/174.24; 252/174.17; 252/542; 252/545; 252/548; 252/DIG. 2; 252/DIG. 1; 252/DIG. 5; 252/DIG. 13; 252/DIG. 14; 424/70
[58] Field of Search ...................... 252/174.21, 174.22, 252/174.23, 174.24, 545, 90, 548, DIG. 2, DIG. 3, DIG. 5, DIG. 13, DIG. 14; 424/70

[56] References Cited

U.S. PATENT DOCUMENTS

| | | | |
|---|---|---|---|
| 3,156,655 | 11/1964 | Bright | 252/109 |
| 3,723,375 | 3/1973 | Field et al. | 424/70 |
| 3,836,637 | 9/1974 | Schmolka | 424/70 |
| 3,969,500 | 7/1976 | Kennerley | 424/10 |
| 4,128,631 | 12/1978 | Lundmark et al. | 424/70 |
| 4,154,706 | 5/1979 | Kenkare et al. | 252/547 |
| 4,284,533 | 8/1981 | Imamura et al. | 252/542 |
| 4,508,635 | 4/1985 | Clarke | 252/174.23 |
| 4,559,159 | 12/1985 | Denzinger et al. | 252/174.24 |

FOREIGN PATENT DOCUMENTS

| | | |
|---|---|---|
| 0007120 | 1/1980 | European Pat. Off. . |
| 0017149 | 10/1980 | European Pat. Off. . |
| 0066342 | 12/1982 | European Pat. Off. . |
| 0089213 | 9/1983 | European Pat. Off. . |
| 2307775 | 8/1973 | Fed. Rep. of Germany . |
| 2277859 | 2/1976 | France . |
| 2380774 | 9/1978 | France . |
| 2403353 | 4/1979 | France . |
| 81699 | 4/1974 | Japan . |
| 122900 | 9/1981 | Japan . |
| 957175 | 5/1964 | United Kingdom . |
| 2050165 | 1/1981 | United Kingdom . |
| 2088209 | 6/1982 | United Kingdom . |
| 2098624A | 11/1982 | United Kingdom . |

*Primary Examiner*—Prince E. Willis
*Attorney, Agent, or Firm*—Fleit, Jacobson, Cohn & Price

[57] ABSTRACT

A washing and foaming composition containing at least one non-ionic surface-active agent which, in 10% aqueous solution, has a detergency which is greater than or equal to that of a 2% aqueous solution of sodium laurylsulphate, together with at least one anionic polymer in proportions such that the ratio of anionic polymer/non-ionic surface-active agent is greater than 0.1:1.

25 Claims, No Drawings

WASHING AND FOAMING COMPOSITION BASED ON NON-IONIC SURFACE-ACTIVE AGENTS AND ANIONIC POLYMERS

The present invention relates to washing and foaming compositions containing non-ionic surface-active agents and anionic polymers, these compositions being intended for treating keratin fibres, and in particular human hair, and the skin.

For many years, non-ionic surface-active agents have been known which, because of their detergency property, are commonly used in shampoo compositions.

Polymers have also already been used in shampoos for the purpose of modifying the properties of the fibres, especially as regards the hold and the ease of combing of the hair.

We have discovered that it is possible considerably to improve the detergency of non-ionic surface-active agents and also the mildness of their foam.

These improvements are such that it is possible, by the addition of anionic polymer(s), to reduce the concentration of surface-active agents in washing and foaming compositions without reducing their detergency, and this is economically advantageous. Furthermore, the compositions are well tolerated by the skin and mucous membranes.

These non-ionic surface-active agents may be of the polyoxyethyleneated, polyglycerolated, polyglycidolated type and polyglycosylated type.

These surprising results are obtained using the said non-ionic surface-active agent or agents and the said anionic polymer or polymers in particular proportions such that the ratio of anionic polymer(s)/non-anionic surface-active agent(s) is at least 0.1:1. Moreover, the compositions should not contain large proportions of cationic derivatives and, in particular, they should not contain cationic polymers.

The present invention therefore relates to new washing and foaming compositions containing at least one non-ionic surface-active agent and at least one anionic polymer as well as to a process for washing or cleaning keratin fibres, and in particular human hair, and the skin, using such compositions.

The washing and foaming compositions according to the invention contain at least one polyoxyethyleneated, polyglycerolated, polyglycidolated or polyglycosylated non-ionic surface-active agent together with at least one anionic polymer, the weight ratio of the anionic polymer to the non-ionic surface-active agent is greater than 0.1:1 and preferably 0.125:1 to 2.25:1.

In 10% aqueous solution, the non-ionic surface-active agents used have a detergency which is greater than or equal to that of a 2% aqueous solution of sodium lauryl-sulphate in the following test.

DETERMINATION OF DETERGENCY

A determined quantity of sebum is deposited on wool samples in the form of a spot. After the samples have been washed under standard conditions in an automatic machine and dried, the residual quantity of sebum is revealed by developing with osmic acid. This gives a spot whose colouration ranges from pale grey to black, according to the quantity of sebum remaining: the darker the spot, the greater the quantity of sebum remaining and the lower the detergency of the composition studied.

The following method is used and all the measurements are carried out in duplicate. 70 mg of artificial sebum having the following composition:

| | |
|---|---|
| 97% squalene | 19% |
| Cholesterol puriss. | 5% |
| Technical-grade triolein | 45% |
| Pure oleic acid | 31% | are applied to a sample of virgin wool. The sample is then washed in an automatic machine consisting essentially of a moving plate, a pressure roller and jets delivering the rinsing water.

When active, the plate is driven with a reciprocating movement at a frequency of 20 passes per minute (+ or −3 seconds).

After the sample has been fixed to the plate, 0.75 ml of the composition to be tested is deposited on the fabric and 60 roller passes are carried out (3 minutes). The sample is then rinsed by dispersing 240 ml of water and moving the plate and roller for 3 minutes (60 passes).

The washing is then repeated with 0.5 ml of the composition to be tested, 60 roller passes and rinsing with 240 ml of water and 120 roller passes (6 minutes).

The residual sebum is developed with osmic acid vapours. In a leaktight box, osmic acid is released and left in contact with the sample for 5 minutes, this period of time being sufficient to complete the reaction with the sebum.

The intensity of the colour of the spot is measured by a visual method, a sodium lauryl-sulphate solution containing X% of sodium lauryl-sulphate being taken as the standard. The intensity of the spot of the composition to be tested is compared with the most similar intensity of the sodium lauryl-sulphate solution. Standard solutions containing varying concentrations of sodium lauryl-sulphate are used for this purpose.

The detergent activity is expressed as equivalents of sodium lauryl-sulphate.

The preferred surface-active agents are glucoside alkyl ethers or condensation products of monoalcohols, α-diols, alkylphenols or alkanolamides with glycidol, glycidol precursors.

The compounds which are particularly valuable and which lead to an improved detergency when they are used in association with anionic polymers are the compounds of the formula:

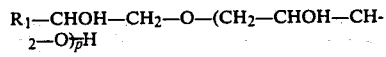

$$R_1-CHOH-CH_2-O-(CH_2-CHOH-CH_2-O)_pH$$

in which $R_1$ denotes an aliphatic, cycloaliphatic or arylaliphatic radical having from 7 to 21 carbon atoms, or a mixture thereof, it being possible for the aliphatic chains to contain ether, thioether or hydroxymethylene groups, and in which p is from 1 to 10, these compounds being described more particularly in French Pat. No. 2,091,516; compounds of the formula:

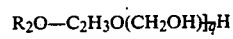

$$R_2O-C_2H_3O(CH_2OH)_qH$$

in which $R_2$ denotes an alkyl, alkenyl or alkylaryl radical and q has an average statistical value of from 1 to 10, these compounds being described more particularly in French Pat. No. 1,477,048; and compounds of the formula:

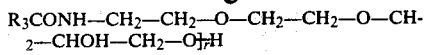

in which $R_3$ denotes a linear or branched, saturated or unsaturated aliphatic radical, or a mixture of such radicals, which can optionally contain one or more hydroxyl groups, has 8 to 30 carbon atoms and is of natural or synthetic origin, and r represents an integer or decimal number from 1 to 5 and denotes the average degree of condensation, these compounds being described more particularly in French Pat. No. 2,328,763.

The non-ionic surface-active agents which give particularly advantageous results in the compositions according to the invention have the formulae:

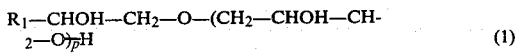 (1)

in which $R_1$ denotes a mixture of alkyl radicals having from 9 to 12 carbon atoms and p has a statistical value of about 3.5;

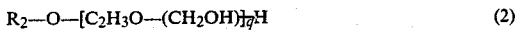 (2)

in which $R_2$ denotes $C_{12}H_{25}$ and q has a statistical value of 4 to 5;

 (3)

in which $R_2$ denotes a mixture of alkyl radicals having 10 to 12 carbon atoms and q has a statistical value of about 3.75;

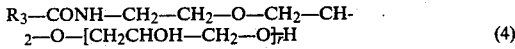 (4)

in which $R_3$ denotes a mixture of radicals derived from lauric, myristic, oleic and copra acids and r has a statistical value of 3 to 4; and

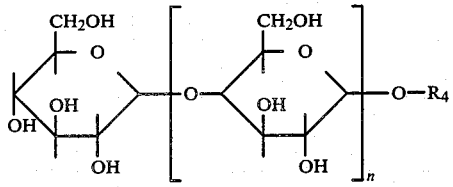

in which $R_4$ denotes an alkyl radical having 8 to 10 carbon atoms and n is equal to 0, 1, 2, 3 or 4, which is sold under the name TRITON CG 110 by SEPPIC.

The anionic polymers used according to the invention are polymers having a molecular weight of from 500 to 6,000,000 and preferably of from 5000 to 1,000,000, and containing carboxylic or sulphonic acid groups.

The carboxylic acid groups are especially derived from unsaturated monocarboxylic or dicarboxylic acids represented by the formula:

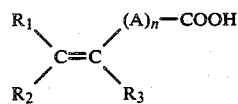

in which n is 0 or an integer from 1 to 10, A denotes a methylene group optionally joined to the carbon atom of the unsaturated group via a heteroatom such as oxygen or sulphur or, if n is greater than 1, the A groups can be optionally interrupted by the said heteroatom, $R_1$ denotes a hydrogen atom or a phenyl or benzyl group, $R_2$ denotes a hydrogen atom or a lower alkyl or carboxyl group and $R_3$ denotes a hydrogen atom, a lower alkyl group, $-CH_2-COOH$ or a phenyl or benzyl group.

In the above formula, the lower alkyl radicals preferably denote a group having from 1 to 4 carbon atoms, such as methyl or ethyl.

Among these polymers, those which are more particularly preferred are acrylic or methacrylic acid homopolymers or copolymers such as the products sold under the name GOODRITE K732 by GOODRITE, VERSICOL E or K by ALLIED COLLOIDS, and ULTRAHOLD 8 by CIBA-GEIGY, the sodium salts of acrylic acid/acrylamide copolymers sold under the name RETEN 421, 423 or 425 by HERCULES, the sodium polymethacrylate sold under the name DARVAN No. 7 by Van der BILT, the polyhydroxycarboxylic acid polymers sold under the name HYDAGEN F by HENKEL, and optionally mono-esterified, unsaturated polymers containing an $\alpha,\beta$ dicarboxylic acid unit, such as the copolymers resulting from the copolymerization of a compound containing a group

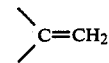

with a compound of the formula:

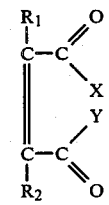

in which $R_1$ and $R_2$ independently of one another denote hydrogen, halogen or a sulphonic acid, alkyl, aryl or aralkyl group, X denotes OH and Y denotes OH, O-alkyl, O-aryl, NH-alkyl, NH-aryl or NH-cycloalkyl, or alternatively X and Y together denote 0 i.e. an anhydride link is present.

There may be mentioned, in particular, unsaturated $\alpha,\beta$-dicarboxylic acids such as maleic, fumaric, itaconic, citraconic, phenylmaleic, benzylmaleic, dibenzylmaleic and ethylmaleic acids or the anhydrides of these acids, such as maleic anhydride, and also other derivatives such as the half-esters of these acids.

Examples which may be mentioned of compounds which can be polymerized and contain a group

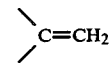

are vinyl esters, vinyl ethers, vinyl halides, phenylvinyl derivatives such as styrene, acrylic acid and its esters, and cinnamic acid esters. These polymers are described in greater detail in, for example, U.S. Pat. No. 2,047,398.

These polymers can optionally be esterified. More particularly valuable compounds are those described in U.S. Pat. Nos. 2,723,248 and 2,102,113 which have units of formula:

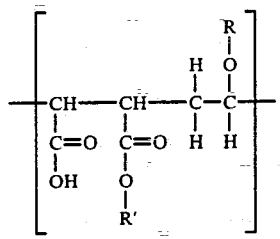

in which R represents an alkyl group having 1 to 4 carbon atoms, such as methyl, ethyl, propyl, isopropyl, butyl or isobutyl, and R' represents an alkyl group having 1 to 8 carbon atoms, such as methyl, ethyl, propyl, butyl, isobutyl, pentyl, hexyl, heptyl, octyl or isooctyl.

Other polymers of this type which can be used according to the invention are copolymers of maleic anhydride and an olefine having from 2 to 4 carbon atoms, which are partially esterified (e.g. 50 to 70%) by an alcohol having from 1 to 4 carbon atoms, these copolymers being described more particularly in British Pat. No. 839,805.

Other copolymers which can be used and which belong to this family are the copolymers resulting from the copolymerization of (a) an unsaturated acid anhydride such as maleic, citraconic or itaconic anhydride, and (b) an allyl or methallyl ester such as allyl or methallyl acetate, propionate, butyrate, hexanoate, octanoate, dodecanoate, octodecanoate, pivalate, neoheptanoate, neooctanoate, neodecanoate, 2-ethylhexanoate, 2,2,4,4-tetramethylvalerate or 2-isopropyl-2,3-dimethylbutyrate. The anhydride groups of these acids are either monoesterified with an aliphatic alcohol such as methanol, ethanol, propanol, isopropanol or n-butanol, or amidified with an aliphatic, cyclic or heterocyclic amine such as propylamine, isopropylamine, butylamine, dibutylamine, hexylamine, dodecylamine, morpholine, piperidine, pyrrolidine or N-methylpiperazine.

It is also possible to use the terpolymers resulting from the copolymerization of the monomers in paragraphs (a) and (b) above with an acrylamide or methacrylamide such as N-tert.-butylacrylamide, N-octylacrylamide, N-decylacrylamide, N-dodecylacrylamide, N-[(1,1-dimethyl)prop-1-yl]acrylamide, N-[(1,1-dimethyl)but-1-yl]acrylamide or N-[(1,1-dimethyl)pent-1-yl]acrylamide or the corresponding methacrylamide, the anhydride groups being esterified or amidified as indicated above.

The copolymers of this type can optionally also be copolymerized with α-olefins such as prop-1-ene, but-1-ene, hex-1-ene, dodec-1-ene, hexadec-1-ene and octadec-1-ene, with vinyl ethers such as methyl vinyl ether, ethyl vinyl ether, propyl vinyl ether, isopropyl vinyl ether, butyl vinyl ether, hexyl vinyl ether, dodecyl vinyl ether, hexadecyl vinyl ether and octadecyl vinyl ether, with acrylic or methacrylic acid esters such as methyl, ethyl, propyl, isopropyl, butyl, tert.-butyl, hexyl, octyl, decyl, dodecyl, octadecyl, 2,3-dihydroxypropyl, ω-methylpolyethylene glycol and ω-ethyl-polyethylene glycol acrylates and methacrylates, and, if appropriate, acrylic or methacrylic acid or N-vinylpyrrolidone in the case of the terpolymers. Polymers of this type are described in, e.g., French Pat. Nos. 2,350,834 and 2,357,241.

Among the polymers belonging to this family, there may also be mentioned the polymers derived from the maleic and itaconic acids and anhydrides mentioned above, and their copolymers with a monoethylenic unsaturated monomer such as ethylene, vinylbenzene, vinyl acetate, vinyl methyl ether or acrylamide, optionally hydrolyzed in the case of the anhydrides.

The polymers which are more particularly preferred are the products sold under the names Gantrez AN 119, 139, 149 and 169, which are maleic anhydride/methyl vinyl ether copolymers (1:1), and Gantrez ES 225, 335, 425 and 435, which are respectively the monoethyl ester, monoisopropyl ester and monobutyl ester of poly(methyl vinyl ether/maleic anhydride), sold by General Aniline, EMA 91, which is the ethylene/maleic anhydride copolymer sold by the MONSANTO COMPANY, EMA 1325, which is the mono-n-butyl (poly)ethylene maleate sold by the MONSANTO COMPANY, and also the product sold under the name Gantrez S 95, which is the hydrolyzed form of poly(methyl vinyl ether/maleic anhydride).

It is also possible to use polyacrylamides containing carboxylate groups, sold especially by American Cyanamid under the name CYANAMER A 370.

Polymers containing sulphonic acid groups which can be used according to the invention are especially polyacrylamidesulphonic acid salts such as those mentioned in U.S. Pat. No. 4,128,631, and more particularly the polyacrylamidoethylpropanesulphonic acid sold under the name COSMEDIA POLYMER HSP 1180 by HENKEL.

These compositions should not contain cationic polymers, which would detract from the desired effect of the anionic polymer.

The total concentration of surface-active agent is suitably 0.5 to 20% and preferably 2 to 8% by weight of active ingredient. The total concentration of anionic polymer is suitably 0.05 to 15% and preferably 1 to 8% by weight of active ingredient. These compositions generally have a pH of 2 to 10 and preferably of 3 to 9. The pH can be adjusted with known alkalizing or acidifying agents normally used in this type of washing composition.

According to the invention, the compositions may also contain anionic surface-active agents. It should be noted, however, that the improvement in detergency afforded by association of the anionic polymer with the non-ionic surface-active agents mentioned above makes it possible to use a much smaller quantity of anionic surface-active agents than it would have been necessary to use in order to have a similar detergency effect in the presence of the same non-ionic surface-active agent. Furthermore, this use of a reduced quantity of anionic surface-active agents makes it possible to prepare shampoos having very good detergency and foaming properties while at the same time being very mild towards the skin.

These surface-active agents are in themselves well known.

The compositions can take various forms normally used for compositions for washing or cleaning the hair or skin, and can be presented especially in the form of aqueous or aqueous-alcoholic solutions which may or may not be thickened, creams, gels, dispersions, emulsions or aerosol foams. In addition to the non-ionic surface-active agent or agents defined above and the anionic polymer or polymers in the proportions indicated, they can contain adjuvants normally used in cosmetics, preferably with the exception of cationic polymers, and especially perfumes, colourants, preservatives, sequestering agents, thickeners, emulsifying agents, softeners, electrolytes, non-ionic polymers, foam stabilizers and the like, according to the application envisaged.

These compositions can be used in the form of shampoos, bath foams, make-up remover compositions for the skin or eyes, or compositions for washing the skin.

The present invention also provides a process for washing and cleaning the skin or hair, which is essentially characterized in that at least one composition of this invention is applied to the hair or skin, and in that, if appropriate, after application, the hair or skin is rinsed with water by the traditional methods used in this field.

The Examples which follow further illustrate the present invention.

EXAMPLE 1

A shampoo having the following composition is prepared:
Non-ionic surface-active agent of the formula:

| | |
|---|---|
| R—CHOH—CH$_2$O—(CH$_2$—CHOH—CH$_2$O)$_n$—H <br> in which R is a mixture of C$_9$-C$_{12}$ alkyl <br> radicals and n represents an average statistical value of about 3.5 | 5 g |
| Methyl vinyl ether/maleic anhydride copolymer <br> sold under the name GANTREZ AN 119 by GENERAL ANILINE and hydrolyzed with sodium hydroxide | 5 g |
| Water, perfume, preservative, colourant q.s. <br> pH = 7 with HCl | 100 g |

This composition has a greater detergency than that corresponding to 10% of surface-active agent in solution in water and at the same pH.

When applied to dirty hair, it develops a very mild foam and washes the hair perfectly. The wet hair is not tangled and the dried hair is bouncy, smooth and shiny.

EXAMPLE 2

A shampoo having the following composition is prepared:
Surface-active agent of the formula:

| | |
|---|---|
| RCHOHCH$_2$O—(CH$_2$—CHOH—CH$_2$O)$_n$—H <br> in which R is a mixture of C$_9$-C$_{12}$ alkyl <br> radicals and n = 3.5 (statistical value) | 5 g |
| Polyacrylic acid having an approximate molecular <br> weight of 1 million, sold as <br> a solution containing 15% of active ingredient (A.I.) <br> in water under the name VERSICOL E13 <br> by ALLIED COLLOIDS | 5 g A.I. |
| Water, perfume, preservative, colourant q.s. <br> pH = 7 with sodium hydroxide | 100 g |

This composition has a greater detergency than that corresponding to 5% of the same surface-active agent.

EXAMPLE 3

The following composition is prepared:
Polyglycerolated fatty diglycolamide:

| | |
|---|---|
| R—CO—NHCH$_2$—CH$_2$—O—CH$_2$—(O—CH$_2$—CHOH—CH$_2$)$_{3.5}$—OH <br> in which R = C$_{11}$-C$_{18}$ natural fatty amides | 5 g AI |
| Polyacrylic acid of approximate molecular weight 230,000, <br> containing 25% of AI (active ingredient), sold under the <br> name VERSICOL E 11 by ALLIED COLLOIDS | 3 g AI |
| Water, perfume, preservative(s), colourant(s) q.s. <br> pH = 6.3 with sodium hydroxide | 100 g |

This composition is used as a shampoo for washing the hair.

EXAMPLE 4

The following composition is prepared:
Non-ionic surface-active agent prepared from a mixture of fatty alcohols:

| | |
|---|---|
| $R-O-\left[\begin{array}{c} CH_2-CH-O \\ \vert \\ CH_2OH \end{array}\right]_n-H$ | 5 g AI |
| in which R = C$_{10}$H$_{21}$/C$_{12}$H$_{25}$ in the molar ratio <br> 54/56 and n̄ = 3.75 | |
| Maleic anhydride/ethylene copolymer sold under <br> the name EMA 91 by MONSANTO (used in the form <br> of the sodium salt after hydrolysis with sodium <br> hydroxide) | 0.6 g AI |
| Water, perfume, colourant(s), preservative(s) <br> pH = 6.6 with hydrochloric acid. | 100 g |

This composition is used as a shampoo.

EXAMPLE 5

The following composition is prepared:
Glucoside alkyl ether sold as a solution containing 30% of AI under the name TRITON CG 110

| | |
|---|---|
| by SEPPIC | 7 g AI |
| Sodium salt of a polyhydroxycarboxylic acid, <br> sold under the name HYDAGEN F by HENKEL | 3 g AI |
| Water, perfume, preservative q.s. <br> pH = 7.0, adjusted with sodium hydroxide. | 100 g |

This composition is used as a shampoo for washing the hair.

EXAMPLE 6

The following composition is prepared:
Glucoside alkyl ether sold as a solution containing 30% of AI under the name TRITON

| | |
|---|---|
| CG 110 by SEPPIC | 8 g AI |
| Modified polyacrylamide sold under the name <br> CYANAMER A 370 by AMERICAN CYANAMID | 2 g AI |
| Water, perfume, preservative q.s. <br> pH = 7.5, adjusted with sodium hydroxide. | 100 g |

This composition is used as a shampoo for washing the hair.

EXAMPLE 7

The following composition is prepared:
Non-ionic surface-active agent of the formula:

| | |
|---|---|
| R—CHOH—CH$_2$O—(CH$_2$—CHOH—CH$_2$O)$_{\overline{n}}$H<br>in which R = mixture of C$_9$-C$_{12}$ alkyl radicals<br>and n = average statistical value of about 3.5 | 5 g |
| COSMEDIA POLYMER HSP 1180 | 1 g |
| Water, perfume, preservative q.s.<br>pH = 3, adjusted with Hydrochloric acid | 100 g |

This composition is used as a shampoo for washing the hair.

EXAMPLE 8

The following composition is prepared:

Glycerolated fatty diglycolamide, in approximately 30% solution, of the formula:

| | |
|---|---|
| R—CO—NHCH$_2$—CH$_2$—O—CH$_2$—CH$_2$—(O—CH$_2$—CHOH—CH$_2$)$_{\overline{3.5}}$—OH<br>in which R = C$_{12}$-C$_{18}$ natural fatty amides | 7 g |
| Modified polyacrylamide sold under the name<br>CYANAMER A 370 by AMERICAN CYANAMID | 3 g |
| Water, perfume, preservative q.s.<br>pH = 7.5, adjusted with triethanolamine | 100 g |

This composition is used as a shampoo for washing the hair.

EXAMPLE 9

The following composition is prepared:

Non-ionic surface-active agent based on polyglycerolated lauryl alcohol (4.2 mol of glycerol), as a solution containing about 60% of active ingredient, of the (statistical) formula:

| | |
|---|---|
| C$_{12}$H$_{25}$—(O—CH$_2$—CH)$_{\overline{4.2}}$—OH<br>                             \|<br>                             HOH$_2$C | 6 g |
| Sodium salt of a polyhydroxycarboxylic acid,<br>sold under the name HYDAGEN F by HENKEL | 4 g |
| Water, perfume, preservative q.s.<br>pH = 7.25, adjusted with hydrochloric acid. | 100 g |

This composition is used as a shampoo for washing the hair.

EXAMPLE 10

The following composition is prepared:

Glucoside alkyl ether sold as a solution containing 30% of AI under the name TRITON

| | |
|---|---|
| CG 110 by SEPPIC | 6 g AI |
| Polymethacrylic acid of approximate MW 10,000,<br>containing 25% of AI, sold under the name<br>VERSICOL K 11 by ALLIED COLLOIDS | 3.2 g |
| Water, perfume, preservative q.s.<br>pH = 7.3, adjusted with hydrochloric acid. | 100 g |

This composition is used as a shampoo for washing the hair.

Table I which follows relates to other examples of the invention.

The compositions of Examples 11 to 15 and 18 to 25 are used as shampoos for washing the hair, the composition of Example 16 is used as a lotion for cleaning the body and the composition of Example 17 is used as a make-up remover for the eyes.

TABLE I

| | Surface-active agent | | Anionic polymer | | | Adjusted |
|---|---|---|---|---|---|---|
| Example | S.A.A. | Concentration % AI | | Concentration % AI | pH | with |
| 11 | S.A.A.1 | 5 | GANTREZ S 95 | 3 | 7 | Hydrochloric acid |
| 12 | S.A.A.1 | 4 | VERSICOL K 11 | 3 | 5.6 | " |
| 13 | S.A.A.2 | 7 | GANTREZ S 95 | 5 | 6.2 | " |
| 14 | S.A.A.3 | 3 | GANTREZ S 95 | 3 | 8.7 | Sodium hydroxide |
| 15 | TRITON CG 110 | 3 | GANTREZ S 95 | 4 | 4.5 | Hydrochloric acid |
| 16 | S.A.A.3 | 3 | DARVAN 7 | 1 | 7.7 | " |
| 17 | S.A.A.2 | 0.5 | GANTREZ ES 425 | 0.5 | 4.9 | " |
| 18 | S.A.A.1 | 5 | RETEN 423 | 5 | 7 | |
| 19 | S.A.A.1 | 9 | GANTREZ S 95 | 1.4 | 7 | |
| 20 | S.A.A.1 | 5 | GANTREZ S 95 | 1 | 7 | |
| 21 | S.A.A.1 | 5 | GANTREZ S 425 | 5 | 7 | |
| 22 | S.A.A.2 | 5 | COSMEDIA POLYMER HSP 1180 | 5 | 7 | |
| 23 | S.A.A.3 | 5 | COSMEDIA POLYMER HSP 1180 | 5 | 7 | |
| 24 | TRITON CG 110 | 5 | COSMEDIA POLYMER HSP 1180 | 5 | 7 | |
| 25 | S.A.A.1 | 5 | GOODRITE K 732 | 5 | 7 | |

In the above table, the tradenames or the abbreviations denote the following products:

| | |
|---|---|
| GANTREZ ES 425 | Monobutyl ester of poly(methyl vinyl ether/maleic acid), sold by GENERAL ANILINE |
| DARVAN 7 | Sodium salt of methacrylic acid homopolymer, sold as a 25% solution by VANDERBILT |
| GANTREZ S 95 | Hydrolyzed poly(methyl vinyl ether/maleic anhydride) sold by GAF |
| VERSICOL K 11 | Methacrylic acid polymer of MW 10,000, sold by ALLIED COLLOIDS |
| RETEN 423 | Acrylamide/sodium acrylate copolymer sold by HERCULES |
| GOODRITE K 732 | Polyacrylic acid of MW 5,000, sold by GOODRITE |
| COSMEDIA POLYMER HSP 1180 | Polyacrylamidomethylpropanesulphonic acid sold containing 15% of AI by HENKEL |
| S.A.A. 1 | Surface-active agent of the formula: |

| | |
|---|---|
| | R—CHOH—CH$_2$—(O—CH$_2$—CHOH—CH$_2$—O)$_{\overline{n}}$H<br>in which R = mixture of C$_9$-C$_{12}$ alkyl radicals and n represents an average statistical value of about 3.5 |
| S.A.A. 2 | Non-ionic surface-active agent based on polyglycerolated lauryl alcohol (4.2 mol of glycerol), as a solution containing 60% of AI, of the statistical formula:<br>C$_{12}$H$_{25}$—(O—CH$_2$—CH)$_{\overline{4.2}}$—OH<br>                                                 HOH$_2$C |
| S.A.A. 3 | Polyglycerolated fatty diglycolamide<br>R—CO—NH—CH$_2$—CH$_2$—O—CH$_2$—CH$_2$—(O—CH$_2$—CHOH—CH$_2$)$_{\overline{3.5}}$—OH<br>in which R = C$_{12}$ to C$_{18}$ natural fatty acid amides |
| TRITON CG 110 | Glucoside alkyl ether sold as a solution containing 30% of AI by SEPPIC. |

We claim:

1. A washing and foaming composition for hair or skin which comprises
in a cosmetically acceptable medium
at least one member selected from the group consisting of polyoxyethyleneated, polyglycerolated, polyglyciodolated and polyglycosylated non-ionic surface-active agents which, as a 10% by weight aqueous solution, has a detergency which is greater than or equal to that of a 2% by weight aqueous solution of sodium laurylsulphate, and
at least one anionic polymer in proportions such that the weight ratio of anionic polymer:non-ionic surface-active agent is greater than 0.1:1, said anionic polymer being a polymer having a molecular weight of from 500 to 6,000,000 and containing carboxylic acid groups or a salt of polyacrylamido sulphonic acid; said composition containing no polymers which carry a cationic group.

2. A composition according to claim 1, in which the weight ratio of anionic polymer:non-ionic surface-active agent is from 0.125:1 to 2.25:1.

3. A composition according to claim 1 in which the non-ionic surface-active agent is selected from the the group consisting of glucoside alkyl ethers, and condensation products of monoalcohols, α-diols, alkylphenols or alkanolamides with glycidol or with glycidol precursors.

4. A composition according to claim 3, in which the non-ionic surface-active agent is selected from the group consisting of:
a product of the formula:

R$_1$—CHOH—CH$_2$—O—(CH$_2$—CHOH—CH$_2$—O)$_{\overline{p}}$H in which R$_1$ denotes an aliphatic, cycloaliphatic or arylaliphatic radical having from 7 to 21 carbon atoms, or a mixture thereof, and p is from 1 to 10;
a product of the formula:

R$_1$—CHOH—CH$_2$—O—(CH$_2$—CHOH—CH$_2$—O)$_{\overline{p}}$H in which R$_1$ denotes an aliphatic, cycloaliphatic or arylaliphatic radical having from 7 to 21 carbon atoms, or a mixture thereof, said aliphatic chains containing at least one ether, thioether or hydroxymethylene group, and p is from 1 to 10;
a product of the formula:

R$_2$O[C$_2$H$_3$O(CH$_2$OH)]$_{\overline{q}}$H in which R$_2$ denotes an alkyl, alkenyl or alkylaryl radical and q has a statistical value of from 1 to 10;
a product of the formula:

R$_3$CONH—CH$_2$—CH$_2$—O—CH$_2$CH$_2$—O—[CH$_2$—CHOH—CH$_2$—O]$_{\overline{r}}$H in which R$_3$ denotes a linear or branched, saturated or unsaturated aliphatic radical, or a mixture of such radicals has 8 to 30 carbon atoms, and r represents an integer or decimal number from 1 to 5 and denotes the average degree of condensation; and
a product of the formula:

R$_3$CONH—CH$_2$—CH$_2$—O—CH$_2$CH$_2$—O—[CH$_2$—CHOH—CH$_2$—O]$_{\overline{r}}$H in which R$_3$ denotes a linear or branched, saturated or unsaturated aliphatic radical, or a mixture of such radicals, said aliphatic radicals containing at least one hydroxyl group, has 8 to 30 carbon atoms, and r represents an integer or decimal number from 1 to 5 and denotes the average degree of condensation.

5. A composition according to claim 4, in which the non-ionic surface-active agent has the formula:

R$_1$—CHOH—CH$_2$—O—[CH$_2$—CHOH—CH$_2$—O]$_{\overline{p}}$H in which R$_1$ denotes a mixture of alkyl radicals having from 9 to 12 carbon atoms and p has a statistical value of about 3.5.

6. A composition according to claim 4, in which the surface-active agent has the formula:

R$_2$—O—[C$_2$H$_3$O—(CH$_2$OH)]$_{\overline{q}}$H in which R$_2$ denotes C$_{12}$H$_{25}$ and q has a statistical value of 4 to 5, or alternatively R$_2$ denotes a mixture of C$_{10}$H$_{21}$ and C$_{12}$H$_{25}$ radicals and q has a statistical value of about 3.75.

7. A composition according to claim 4, in which the non-ionic surface-active agent has the formula:

R$_3$—CONH—CH$_2$—CH$_2$—O—CH$_2$—CH$_2$—O—[CH$_2$CHOH—CH$_2$—O]$_{\overline{r}}$H in which R$_3$ denotes a mixture of radicals derived from lauric, myristic, oleic and copra acids and r has a statistical value of 3 to 4.

8. A composition according to claim 3, in which the non-ionic surface-active agent is a glucoside alkyl ether of the formula:

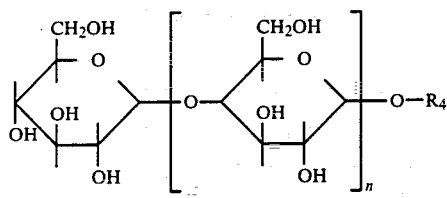

in which $R_4$ denotes an alkyl radical having 8 to 10 carbon atoms and n is equal to 0, 1, 2, 3 or 4.

9. A composition according to claim 1, in which the anionic polymer is a polymer derived from an unsaturated monocarboxylic or dicarboxylic acid selected from the group consisting of:

a product of the formula:

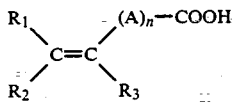

in which n is 0 or an integer from 1 to 10, A denotes a methylene group, $R_1$ denotes a hydrogen atom or a phenyl or benzyl group, $R_2$ denotes a hydrogen atom or a lower alkyl or carboxyl group and $R_3$ denotes a hydrogen atom, a lower alkyl group, a —$CH_2$—COOH group or a phenyl or benzyl group;

a product of the formula:

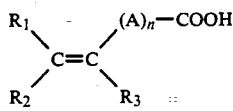

in which n is 0 or an integer from 1 to 10, A denotes a methylene group which is joined to the carbon atom of the unsaturated group via a heteroatom which is an oxygen or a sulfur atom, $R_1$ denotes a hydrogen atom or a phenyl or benzyl group, $R_2$ denotes a hydrogen atom or a lower alkyl or carboxyl group and $R_3$ denotes a hydrogen atom, a lower alkyl group, a —$CH_2$—COOH group or a phenyl or benzyl group;

a product of the formula:

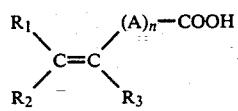

in which n is an integer from 2 to 10, A denotes a methylene group, said A groups being connected via a heteroatom which is an oxygen or a sulfur atom, $R_1$ denotes a hydrogen atom or a phenyl or benzyl group, $R_2$ denotes a hydrogen atom or a lower alkyl or carboxyl group and $R_3$ denotes a hydrogen atom, a lower alkyl group, a —$CH_2$—COOH group or a phenyl or benzyl group; and a product of the formula:

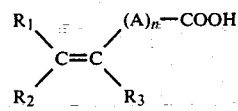

in which n is an integer from 2 to 10, A denotes a methylene group which is joined to the carbon atom of the unsaturated group via a heteroatom which is an oxygen or a sulfur atom, said A groups being connected via a heteroatom which is an oxygen or sulfur atom, $R_1$ denotes a hydrogen atom or a phenyl or benzyl group, $R_2$ denotes a hydrogen atom or a lower alkyl or carboxyl group and $R_3$ denotes a hydrogen atom, a lower alkyl group, a —$CH_2$—COOH group or a phenyl or benzyl group.

10. A composition according to claim 9, wherein the anionic polymer is selected from the group consisting of acrylic or methacrylic acid homopolymers, acrylic or methacrylic acid copolymers, acrylamide carboxylic acid copolymers, polyhydroxycarboxylic acid polymers, polymers derived from unsaturated α,β dicarboxylic acids selected from the group consisting of maleic, fumaric, iraconic, citraconic, phenylmaleic, benzylmaleic, dibenzylmaleic and ethylmaleic acids or derived from the anhydrides of said acids or derived from half-esters of said acids.

11. A composition according to claim 1, in which the anionic polymer is a salt of a polyacrylamidesulphonic acid.

12. A composition according to claim 10, wherein said anionic polymer is copolymerized with a compound containing a

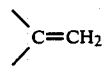

group selected from the group consisting of ethylene, vinyl, allyl and methallyl esters, vinyl ethers, vinyl halides, phenylvinyl derivatives, acrylic acid, methacrylic acid and esters thereof, cinnamic acid esters substituted or unsubstituted acrylamides and methacrylamides, α-olefins, N-vinylpyrrolidone and cinnamic acid esters.

13. A composition according to claim 1, in which the surface-active agent is present in an amount of from 0.5 to 20% by weight.

14. A composition according to claim 13, in which the surface-active agent is present in an amount of from 2 to 8% by weight.

15. A composition according to claim 1, in which the anionic polymer is present in an amount of from 0.05 to 15% by weight.

16. A composition according to claim 15, in which the anionic polymer is present in an amount of from 1 to 8% by weight.

17. A composition according to claim 1, which has a pH of from 2 to 10.

18. A composition according to claim 1 which also contains an anionic surface-active agent.

19. A composition according to claim 1, which is in a form selected from the group consisting of an aqueous or aqueous-alcoholic solution, a thickened aqueous or aqueous-alcoholic solution, a cream, a gel, a dispersion, an emulsion and an aerosol foam.

20. A washing and foaming composition for skin or hair consisting essentially of
  (i) a cosmetically acceptable medium;
  (ii) a member selected from the group consisting of a polyoxyethyleneated non-ionic surface-active agent, a polyglycerolated non-ionic surface-active agent, a polyglycidolated non-ionic surface-active agent and a polyglycosylated non-ionic surface-active agent which, as a 10% by weight aqueous solution, has a detergency which is greater than or equal to that of a 2% by weight aqueous solution of sodium laurylsulphate; and
  (iii) an anionic polymer in a proportion such that the weight ratio of anionic polymer:non-ionic surface-active agent is greater than 0.1:1; said anionic polymer being a polymer having a molecular weight of from 500 to 6,000,000 and containing carboxylic acid groups or a salt of polyacrylamido sulphonic acid.

21. A composition comprising:
  the composition of claim 20; and
  an anionic surface-active agent.

22. A composition comprising:
  the composition of claim 20; and
  a cosmetically acceptable adjuvant, said adjuvant being other than a polymer carrying cationic groups.

23. A process for washing or cleaning hair or skin which comprises applying thereto at least a composition comprising in a cosmetically acceptable medium at least one member selected from the group consisting of polyoxyethyleneated, polyglycerolated, polyglycidolated and polyglycosylated non-ionic surface-active agents which, as a 10% by weight aqueous solution, has a detergency which is greater than or equal to that of a 2% by weight aqueous solution of sodium laurylsulphate, and at least one anionic polymer, in 24. The process of claim 23 wherein the composition contains a surface-active agent selected from the group consisting of
  a product of the formula $R_1$—CHOH—CH$_2$—O—(CH$_2$—CHOH—CH$_2$—O)$_p$H wherein $R_1$ is a (C$_7$–C$_{21}$)aliphatic, cycloaliphatic or arylaliphatic radical or a mixture thereof, and p is from 1 to 10;
  a product of the formula $R_1$—CHOH—CH$_2$—O—(CH$_2$—CHOH—CH$_2$—O)$_p$H wherein $R_1$ is a (C$_7$–C$_{21}$)aliphatic, cycloaliphatic or arylaliphatic radical or a mixture thereof, said aliphatic chains containing at least one ether, thioethero or hydroxymethylene group, and p is 1 to 10;
  a product of the formula $R_2O(C_2H_3O(CH_2OH))_qH$ wherein $R_2$ is alkyl, alkenyl or alkylaryl, and q has a statistical value of from 1 to 10;
  a product of the formula $R_3CONH$—CH$_2$—CH$_2$—O—CH$_2$CH$_2$—O—(CH$_2$—CHOH—CH$_2$—O—)$_p$H wherein $R_3$ is a linear or branched, saturated or unsaturated (C$_8$–C$_{30}$)aliphatic radical or a mixture thereof, and r is an integer or decimal number from 1 to 5 and denotes the average degree of condensation; and
  a product of the formula $R_3CONH$—CH$_2$—CH$_2$—O—CH$_2$CH$_2$—O—(CH$_2$—CHOH—CH$_2$—O—)$_r$H wherein $R_3$ is a linear or branched, saturated or unsaturated (C$_8$—C$_{30}$)aliphatic radical or a mixture thereof, said aliphatic radicals containing at least one hydroxyl group, and r is an integer or decimal number from 1 to 5 and denotes the average degree of condensation.

25. The process of claim 23 wherein the anionic polymer is a polymer derived from an unsaturated monocarboxylic or dicarboxylic acid selected from the group consisting of:
  a product of the formula

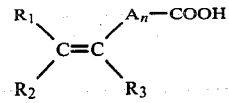

wherein
  n is 0 or an integer from 1 to 10;
  A is methylene;
  $R_1$ is hydrogen, phenyl or benzyl;
  $R_2$ is hydrogen, lower alkyl or carboxyl; and
  $R_3$ is hydrogen, lower alkyl, —CH$_2$—COOH, phenyl or benzyl;
  a product of the formula

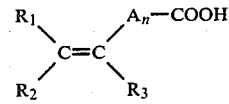

wherein
  n is 0 or an integer from 1 to 10,
  A is a methylene group which is joined to the carbon atom of the unsaturated group via a heteroatom which is an oxygen or a sulfur atom;
  $R_1$ is hydrogen, phenyl or benzyl;
  $R_2$ is hydrogen, lower alkyl or carboxyl;
  $R_3$ is hydrogen, lower alkyl, —CH$_2$—COOH, phenyl or benzyl;
  a product of the formula

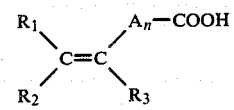

wherein
  n is an integer from 2 to 10;
  A is methylene, said A groups being connected via a heteroatom which is an oxygen or a sulfur atom;
  $R_1$ is hydrogen, phenyl or benzyl;
  $R_2$ is hydrogen, lower alkyl or carboxyl; and
  $R_3$ is hydrogen, lower alkyl, —CH$_2$—COOH, phenyl or benzyl; and
  a product of the formula

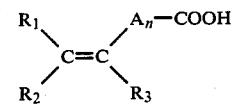

wherein
  n is an integer from 2 to 10,
  A is methylene which is joined to the carbon atom of the unsaturated group via a heteroatom which is an oxygen or a sulfur atom, said A groups being connected via a heteroatom which is an oxygen or a sulfur atom,
  $R_1$ is hydrogen, phenyl or benzyl;
  $R_2$ is hydrogen, lower alkyl or carboxyl;
  $R_3$ is hydrogen lower alkyl, —CH$_2$—COOH, phenyl or benzyl.

* * * * *